(12) United States Patent
Kita et al.

(10) Patent No.: US 9,138,301 B2
(45) Date of Patent: Sep. 22, 2015

(54) MEDICAL DEVICE AND SURFACE MODIFICATION METHOD FOR MEDICAL DEVICE

(75) Inventors: Koichi Kita, Cambridge, MA (US); Komei Kato, Saitama (JP); Akiko Yamamoto, Tsukuba (JP); Junzo Tanaka, Tsukuba (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 461 days.

(21) Appl. No.: 12/095,940

(22) PCT Filed: Dec. 5, 2006

(86) PCT No.: PCT/JP2006/324286
§ 371 (c)(1),
(2), (4) Date: Jun. 3, 2008

(87) PCT Pub. No.: WO2007/066669
PCT Pub. Date: Jun. 14, 2007

(65) Prior Publication Data
US 2009/0162235 A1    Jun. 25, 2009

(30) Foreign Application Priority Data

Dec. 5, 2005 (JP) ................................ 2005-350666
Dec. 5, 2005 (JP) ................................ 2005-350667

(51) Int. Cl.
*A61C 8/00* (2006.01)
*A61F 2/30* (2006.01)
(Continued)

(52) U.S. Cl.
CPC ........... *A61C 8/0012* (2013.01); *A61F 2/30767* (2013.01); *A61L 27/30* (2013.01); *A61L 27/56* (2013.01); *A61C 8/0013* (2013.01); *A61C 2008/0046* (2013.01); *A61F 2/3094* (2013.01);
(Continued)

(58) Field of Classification Search
CPC .............................. A61C 8/0012; A61L 27/34
USPC ......................................................... 433/201.1
IPC ....................................................... C23C 28/321
See application file for complete search history.

(56) References Cited

U.S. PATENT DOCUMENTS 3,855,638 A    12/1974  Pilliar
6,849,230 B1    2/2005  Feichtinger
(Continued)

FOREIGN PATENT DOCUMENTS

EP    0 523 372 A1    1/1993
EP    523372 A1 *    1/1993
(Continued)

OTHER PUBLICATIONS

"Hormonic Biomaterial-Kaimen Seigyogata Seitai Chowa Zairyo Sosei no Kanosei—Jun Titan Takoshitsu Usuita no Saibo Tekigosei Oyobi Saibo Shinnyusei Hyoka" by Yamamoto et al., The Japan Institute of Metals Koen Gaiyo, Mar. 2006, vol. 138, p. 108.
(Continued)

*Primary Examiner* — Weiping Zhu
(74) *Attorney, Agent, or Firm* — Leason Ellis LLP.

(57) ABSTRACT

The invention provides a medical device in which a metallic porous body is joined to at least a part of a surface of the main body of a medical device, and a surface modification method for the medical device. The metallic porous body is formed in multilayers.

8 Claims, 11 Drawing Sheets

(51) Int. Cl.
*A61L 27/30* (2006.01)
*A61L 27/56* (2006.01)
*A61F 2/32* (2006.01)
*A61F 2/36* (2006.01)
*A61F 2/38* (2006.01)
*A61F 2/40* (2006.01)

(52) U.S. Cl.
CPC .... *A61F 2/32* (2013.01); *A61F 2/36* (2013.01); *A61F 2/367* (2013.01); *A61F 2/3676* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4059* (2013.01); *A61F 2/4081* (2013.01); *A61F 2002/30011* (2013.01); *A61F 2002/3092* (2013.01); *A61F 2002/30322* (2013.01); *A61F 2002/30451* (2013.01); *A61F 2002/30878* (2013.01); *A61F 2002/30894* (2013.01); *A61F 2002/30929* (2013.01); *A61F 2002/30957* (2013.01); *A61F 2002/30968* (2013.01); *A61F 2002/30971* (2013.01); *A61F 2002/30981* (2013.01); *A61F 2002/3813* (2013.01); *A61F 2002/3822* (2013.01); *A61F 2002/3831* (2013.01); *A61F 2002/4018* (2013.01); *A61F 2002/4051* (2013.01); *A61F 2002/4062* (2013.01); *A61F 2002/4077* (2013.01); *A61F 2220/0058* (2013.01); *A61F 2250/0023* (2013.01); *A61F 2250/0026* (2013.01); *A61F 2310/00017* (2013.01); *A61F 2310/00023* (2013.01); *A61F 2310/00029* (2013.01); *A61F 2310/00179* (2013.01); *A61F 2310/00401* (2013.01); *A61F 2310/00407* (2013.01); *A61F 2310/00413* (2013.01); *A61F 2310/00491* (2013.01); *A61F 2310/00544* (2013.01)

(56) References Cited

U.S. PATENT DOCUMENTS

2003/0153981 A1  8/2003  Wang et al.
2005/0048193 A1  3/2005  Li et al.
2005/0100578 A1  5/2005  Schmid et al.

FOREIGN PATENT DOCUMENTS

| EP | 0 566 427 A2 | 10/1993 |
|---|---|---|
| EP | 566427 A2 * | 10/1993 |
| EP | 1633010 A1 | 3/2006 |
| JP | 04-141163 A | 5/1992 |
| JP | A-06-007388 | 1/1994 |
| JP | 7-184987 A | 7/1995 |
| JP | 10-155823 A | 6/1998 |
| JP | 11-276510 A | 10/1999 |
| JP | A-2002-320667 | 11/2002 |
| JP | A-2002-541984 | 12/2002 |
| JP | 2003-509584 A | 3/2003 |
| JP | A-2003-094109 | 4/2003 |
| JP | B-3445301 | 6/2003 |
| JP | B-3445301 | 9/2003 |
| JP | 2004-075532 A | 3/2004 |
| JP | A-2004-141234 | 5/2004 |
| JP | 2004-315909 A | 11/2004 |
| JP | 2004-346411 A | 12/2004 |
| JP | 2005-290482 A | 10/2005 |
| WO | WO 00/64504 | 11/2000 |
| WO | WO-2004/100295 A1 | 11/2004 |

OTHER PUBLICATIONS

Office Action mailed Apr. 26, 2013 for the corresponding European Application No. 06834041.3.

European Search Report mailed Apr. 27, 2012 for the corresponding European Application No. 06834041.3.

Tuchinskiy, Novel Fabrication Technology for Metal Foams, Journal of Advanced Materials, Jul. 2005, pp. 60-65, vol. 37, No. 3.

Wada, Porous Metals for Formed by Slurry Foaming Method, Chemistry & Chemical Industry, Jul. 2001, pp. 811-813, vol. 54, No. 7.

Japanese Office Action mailed Jul. 26, 2011 for the corresponding Japanese patent application No. 2005-350666.

Japanese Office Action mailed Jul. 26, 2011 for the corresponding Japanese patent application No. 2005-350667.

* cited by examiner

MEDICAL DEVICE AND SURFACE MODIFICATION METHOD FOR MEDICAL DEVICE

CROSS REFERENCE TO RELATED APPLICATIONS

This is a U.S. national phase application under 35 U.S.C. §371 of International Patent Application No. PCT/JP2006/324286, filed Dec. 5, 2006 and claims the benefit of Japanese Patent Application No. 2005-350666, filed Dec. 5, 2005, and Japanese Patent Application No. 2005-350667, filed Dec. 5, 2005 the contents of which are incorporated herein in their entirety. The International Application was published on Jun. 14, 2007 as International Publication No. WO 2007/066669 under PCT Article 21(2).

TECHNICAL FIELD

The present invention relates to a medical device and a surface modification method for the medical device.

BACKGROUND OF THE INVENTION

A medical device such as an artificial dental root or an artificial hip joint, which is used by being implanted into a living body, is required to have excellent compatibility and high connectivity with the surrounding living tissue in the living body.

Since surface properties of the medical device have a great effect on these characteristics, various surface modification methods of providing desirable shapes and characteristics to a surface of the medical device have been proposed.

For example, in Japanese Unexamined Patent Application Publication No. 2002-320667 (Patent Literature 1), a medical device is produce in which a surface of a medical device constituted by a porous metallic body is formed from a porous metal powder sintered to a porous state having countless numbers of pores opened to a surface. Further, in JP-A-2004-141234 (Patent Literature 2), a surface modification method is proposed by which a porous layer made by sintering and combining spherical metal particles is attached to a surface of the main body of a medical device.

Moreover, various surface modification methods, by which a medical device surface modification member having high connectivity with preliminarily formed living tissue is joined to a surface of the main body of a medical device, origin characteristics of a medical device are not damaged, and the high connectivity with the surrounding living tissue is maintained, have been examined. Such medical device surface modification member is disclosed in JP-A-6-7388 (Patent Literature 3), JP-A-7-184987 (Patent Literature 4), JP-A-10-155823 (Patent Literature 5), JP-A-2003-94109 (Patent Literature 6), Japanese Patent Application National Publication (Laid-Open) No. 2002-541984 (Patent Literature 7), and Japanese Patent No. 3445301 (Patent Literature 8).

SUMMARY OF THE INVENTION

However, according to the examination of the inventors of the invention, it is difficult to obtain properly high connectivity between a medical device and its surrounding living tissue through a direct medical device surface modification method. In addition, when using a method of joining a conventionally-proposed medical device surface modification member to the main body of a medical device, it is difficult to simultaneously satisfy both the connectivity between the medical device and its surrounding living tissue and a joining strength between and the medical device surface modification member.

In order to obtain a high connectivity with a living tissue, the surface modification member is required to be a porous member having a sufficient void volume (with a high porosity) so that cells which form the living tissue around an implanting portion of the medical device are easily penetrated into the surface modification member.

In order to obtain the high joining strength to the main body of a medical device, it is important to secure a sufficient joining area in a joining surface between the surface modification member and the main body of a medical device.

Accordingly, through the method of sintering a material such as a metal powder described in Patent Literatures 1 and 2, it is difficult to control a pore diameter and a porosity of a metallic porous body formed by sintering. As a result, a penetration property of the cells into the porous body is reduced, and thus the connectivity between the medical device and the living tissue becomes insufficient.

In addition, the joining strength between the metallic porous body and the main body of a medical device is reduced through the method described in Patent Literature 3 to 8, when the porosity of the metallic porous body is increased to improve the connectivity with the living tissue. Accordingly, both the joining strength and connectivity cannot be sufficiently obtained.

Moreover, the main body of a medical device is various in shape according to product specifications or individual differences. Accordingly, in order to deal with such the main body of a medical device having various surface shapes, a method must be provided by which the medical device surface modification member itself has sufficient deformability and the surface modification member is joined to the main body of a medical device with a sufficient strength.

The invention is contrived to solve the problems, and an object of the invention is to provide a medical device having excellent connectivity with living tissue by being able to join a metallic porous body in which a metallic porous thin plate is multilayered as a medical device surface modification member having excellent connectivity with the living tissue to a surface of the main body of a medical device with a high joining strength, and to provide a surface modification method for the medical device by which the connectivity of the medical device with the living tissue can be substantially improved by being able to easily join the metallic porous body to the surface of the main body of a medical device having various surface shapes.

SUMMARY OF THE INVENTION

The inventors of the invention found, after their extensive studies, that the problems are solved by joining a specific metallic porous body to a surface of the main body of a medical device, thereby completing the invention.

A first aspect of the invention provides a medical device in which a metallic porous body is joined to at least a part of a surface of the main body of a medical device. The metallic porous body is formed in multilayers.

It is preferable that the metallic porous body is a metallic porous body in which a metallic porous thin plate prepared by molding a slurry containing a metal powder into a sheet shape, drying the slurry, and defatting and sintering the resulting compact is multilayered. It is preferable that the metallic porous thin plate includes a metallic porous thin plate prepared by molding a slurry containing a metal powder and a foaming agent into a sheet shape, subjecting the slurry to a foaming process, drying the slurry, and defatting and sintering the resulting compact.

It is preferable that a porosity of the metallic porous thin plate is in the range of 40 to 97%. Further, it is preferable that the porosity of the metallic porous thin plate joining to the main body of a medical device is lower than the porosity of the metallic porous thin plate coming in contact with living tissue.

It is preferable that a metal of the metal powder includes at least one of pure titanium, a titanium alloy, stainless steel, a cobalt chrome alloy, tantalum, niobium, and an alloy thereof. Further, it is preferable that the metal of the metal powder is the same kind as used for the main body of a medical device.

A surface of a skeleton including a sintered body of the metal powder of the metallic porous thin plate may be covered with an inorganic compound having biocompatibility.

A second aspect of the invention provides a medical device including a metallic porous thin plate prepared by molding a slurry containing a metal powder and a foaming agent into a sheet shape, subjecting the slurry to a foaming process, drying the slurry, and defatting and sintering the resulting compact. The metallic porous thin plate is deformed to follow at least a part of a surface shape of the main body of a medical device and joined thereto.

It is preferable that the slurry is molded into a sheet shape by a doctor blade method.

A third aspect of the invention provides a surface modification method for a medical device. The method includes preparing a metallic porous thin plate by molding a slurry containing a metal powder into a sheet shape, drying the slurry, and defatting and sintering the resulting compact; preparing a metallic porous body by forming the metallic porous thin plate into multilayers; and deforming the metallic porous body to match at least a part of a surface shape of the main body of a medical device and joining it thereto. Further, it is preferable that the metallic porous thin plate includes a metallic porous thin plate prepared by molding a slurry containing a metal powder and a foaming agent into a sheet shape, subjecting the slurry to a foaming process, drying the slurry, and defatting and sintering the resulting compact.

It is preferable that the slurry is molded into a sheet shape by the doctor blade method.

It is preferable that the joining is diffusion joining.

Further, a fourth aspect of the invention provides a surface modification method for a medical device. The method includes preparing a metallic porous thin plate by molding a slurry containing a metal powder and a foaming agent into a sheet shape, subjecting the slurry to a foaming process, drying the slurry, and defatting and sintering the resulting compact; and deforming the metallic porous thin plate to match at least a part of a surface shape of the main body of a medical device and joining it thereto.

It is preferable that the slurry is molded into a sheet shape by the doctor blade method.

It is preferable that a surface shape of a joining surface of the metallic porous thin plate to the main body of a medical device is asymmetric with respect to a surface shape of a contacting surface of the metallic porous thin plate with living tissue.

It is preferable that a porosity of the metallic porous thin plate is in the range of 50 to 97%. Further, it is preferable that the porosity of the joining surface to the main body of a medical device is lower than the porosity of the contacting surface with the living tissue.

It is preferable that the joining is diffusion joining.

It is preferable that a metal of the metal powder includes at least one of pure titanium, a titanium alloy, stainless steel, a cobalt chrome alloy, tantalum, niobium, and an alloy thereof. Further, it is preferable that the metal of the metal powder is the same kind as used for the main body of a medical device.

Before and/or after the joining, a surface of a skeleton including a sintered body of the metal powder of the metallic porous thin plate may be covered with an inorganic compound having biocompatibility.

'Medical device' means a medical device including: the main body of a medical device; and a metallic porous body in which a metallic porous thin plate is multilayered as a medical device surface modification member and which is joined to at least a part of a surface of the main body of a medical device. For example, the medical device includes an artificial prosthetic member which is widely used by being implanted into a body, such as a bone prosthetic member which has a portion such as an artificial dental root or an artificial hip joint coming in contact with hard tissue such as a bone or a joint of a human body.

'Surface modification of a medical device' means that characteristics of a surface of the main body of a medical device are varied by joining a metallic porous body thereto.

According to the invention, a medical device having excellent connectivity with living tissue can be provided by being able to join a metallic porous body in which a metallic porous thin plate is multilayered as a medical device surface modification member having excellent connectivity with the living tissue to a surface of the main body of a medical device with a high joining strength. Further, a surface modification method for the medical device by which the connectivity of the medical device with the living tissue can be substantially improved can be provided by being able to easily join the metallic porous thin plate as the medical device surface modification member having a high joining strength and excellent connectivity with the living tissue to the surface of the main body of a medical device having various surface shapes.

DETAILED DESCRIPTION OF THE INVENTION

Medical Device Main Body

An example of the main body of a medical device is an artificial prosthetic member which is widely used by being implanted into a body and made of: a material without a hazardous effect on against a living body, such as a metal including stainless steel, a cobalt chrome alloy, titanium, and a titanium alloy; ceramics; or the like.

'Medical device main body' means that a metallic porous thin plate according to the invention is not joined to an artificial prosthetic member. The main body of a medical device includes another medical device surface modification member or the like is provided thereon.

In a medical device according to the invention, the above-described metallic porous body is joined to at least a part of a surface of the main body of a medical device. The above-described metallic porous thin plate may be joined to the whole or a part of the surface of the main body of a medical device for a variety of purposes.

<<Medical Device>>

The medical device according to the invention is a medical device in which the metallic porous body is joined to at least a part of the surface of the main body of a medical device. The metallic porous body is formed in multilayers.

It is preferable that the metallic porous body is a metallic porous body in which the metallic porous thin plate is prepared by molding a slurry containing a metal powder into a sheet shape, drying the slurry, and defatting and sintering the resulting compact is multilayered. It is more preferable that the metallic porous thin plate includes a metallic porous thin plate prepared by molding a slurry containing a metal powder and a foaming agent into a sheet shape using a doctor blade method, subjecting the slurry to a foaming process, drying the slurry, and defatting and sintering the resulting compact.

Examples of the medical device provided according to the invention include: a prosthetic device for hard tissue such as an artificial hip joint, an artificial elbow joint, an artificial knee joint, an artificial shoulder joint, an artificial dental root, an artificial corpus vertebrae, and a bone prosthetic member; a prosthetic device for soft tissue, such as a ligament, or for soft tissue and hard tissue; and a device which facilitates tissue regeneration by preliminarily sowing and culturing cells outside the living body.

Examples of the medical device according to an embodiment of the invention are illustrated in FIG. 6.

Figure 6A:
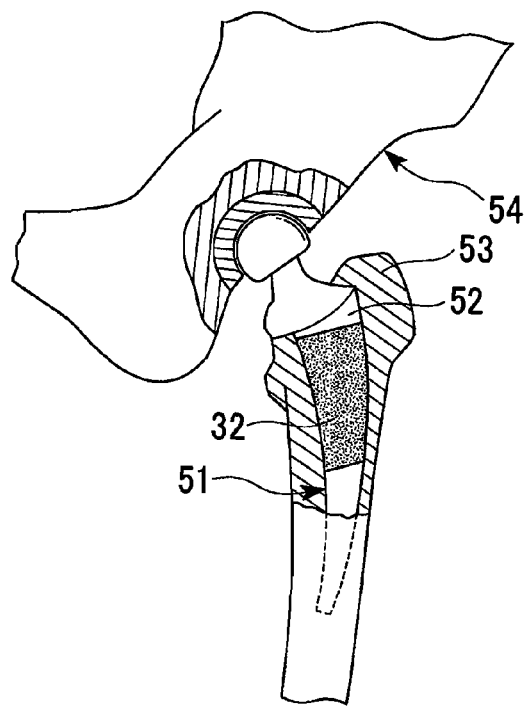
FIG. 6A is a schematic view of an artificial hip joint, illustrating an embodiment of a medical device.

FIG. 6A is a schematic view illustrating an artificial hip joint 51 in which a metallic porous thin plate 21 according to the invention is joined to a surface of a femur stem 52 and is inserted into a medullary cavity of a femur 53 and fixed to a pelvis 54.

Figure 6B:
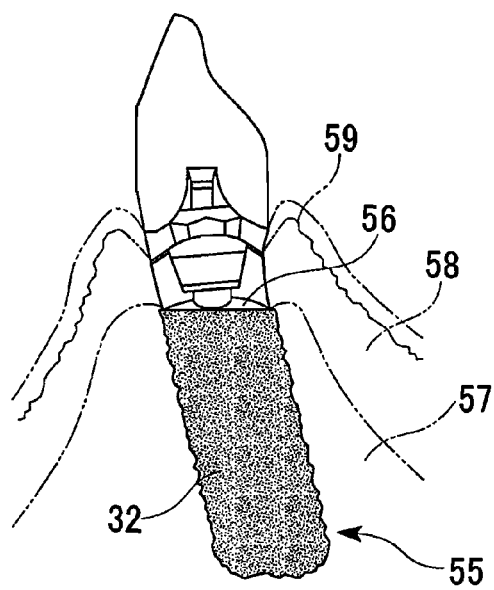
FIG. 6B is a schematic view of an artificial dental root, illustrating an embodiment of the medical device.

FIG. 6B is a schematic view illustrating an artificial dental root 55 in which the metallic porous thin plate 21 according to the invention is joined to a surface of an interlining 56 and is inserted into an alveolar bone 57. In the figure, reference numeral 58 represents connective tissue, and reference numeral 59 represents an epithelium.

Figure 6C:
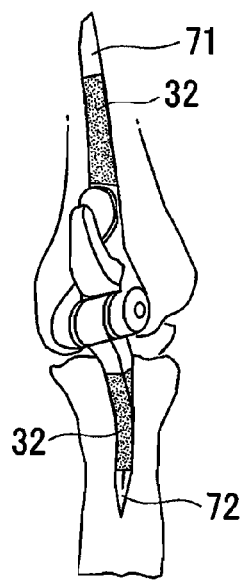
FIG. 6C is a schematic view of an artificial elbow joint, illustrating an embodiment of the medical device

FIG. 6C is a schematic view illustrating an artificial elbow joint in which the metallic porous thin plate 21 according to the invention is joined to surfaces of a humerus stem 71 and an ulna stem 72 and is inserted into a humerus and an ulna, and fixed thereto.

Figure 6D:
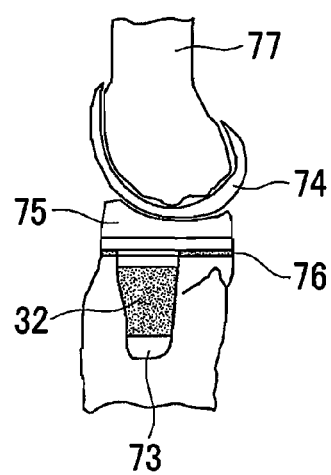
FIG. 6D is a schematic view of an artificial knee joint, illustrating an embodiment of the medical device.

FIG. 6D is a schematic view illustrating an artificial knee joint in which the metallic porous thin plate 21 according to the invention is joined to a surface of a tibia stem 73 and is inserted into a tibia and fixed thereto. In the figure, reference numeral 74 represents an artificial femur head (knee joint side), reference numeral 75 represents a joint sliding portion, reference numeral 76 represents a base plate, and reference numeral 77 represents a femur.

Figure 6E:
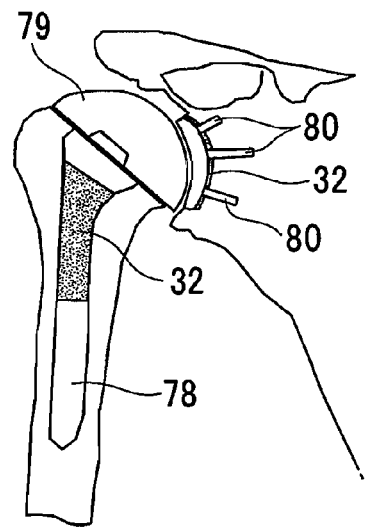
FIG. 6E is a schematic view of an artificial shoulder joint, illustrating an embodiment of the medical device.

FIG. 6E is a schematic view illustrating an artificial shoulder joint in which the metallic porous thin plate 21 according to the invention is joined to a surface of a humerus stem 78 and is inserted into a humerus and fixed thereto while being connected with an artificial humerus head. In the figure, reference numeral 79 represents the artificial humerus head, and reference numeral 80 represents an artificial joint pin.

The medical device which can be substantially improved in connectivity with the living tissue can be provided by easily joining the metallic porous thin plate as a medical device surface modification member having excellent connectivity with the living tissue to the surface of the main body of a medical device having various surface shapes with a high joining strength.

The medical device can use the metallic porous thin plate having a higher porosity than a similar metallic porous body prepared by a conventional sintering method, such as etching and punching, or the like, has the excellent connectivity with the living tissue, has high cell penetration and proliferation rates, and has excellent connectivity with soft tissue as well as hard tissue.

Further, the medical device has a better joining strength to the main body of a medical device, and can be prepared at a lower cost than a conventional medical device.

Peeling of the medical device surface modification member (metallic porous thin plate) from the main body of a medical device, which occurs after the medical device is implanted into the body, problems caused by insufficient connectivity with the living tissue, or the like is reduced, and the use for a longer period of time in the body can be achieved.

In addition, the metallic porous thin plate can be applied to a variety of location of the main body of a medical device.

It is expected that QOL (Quality of Life) of patients is improved and medical expenses are reduced, as describe above.

(Metallic Porous Body)

The metallic porous body is formed in multilayers.

A layer is not particularly limited if it allows advantages of the invention to be obtained. It is preferable that the layer is molded into a sheet shape, and it is more preferable that the layer is the metallic porous thin plate.

It is preferable that the metallic porous thin plate is prepared by molding the slurry containing the metal powder into a sheet shape, drying the slurry, and defatting and sintering the resulting compact in order to improve the connectivity with the main body of a medical device. In addition, it is more preferable that the metallic porous thin plate includes a metallic porous thin plate prepared by molding the slurry containing the metal powder and the foaming agent into a sheet shape, subjecting the slurry to the foaming process, drying the slurry, and defatting and sintering the resulting compact from the viewpoint of improvement of the connectivity with the living tissue.

Hereinafter, the metallic porous thin plate which is preferably used will be described.

The metallic porous thin plate is prepared by molding and processing the slurry containing the metal powder.

The slurry (hereinafter, may be referred to as 'slurry S') contains at least the metal powder, and preferably contains the foaming agent, an aquaresin, and water. If necessary, the slurry contains another component such as a plasticizing agent or an organic solvent.

The prepared metallic porous thin plate has a three-dimensional net-like cell structure. The skeleton of the metallic porous thin plate is formed from the metal powder.

It is preferable that a powder of metal without the hazardous effect on the living body or oxides thereof is used as the metal powder.

It is preferable that the metal of the metal powder is at least one of pure titanium, a titanium alloy, stainless steel, a cobalt chrome alloy, tantalum, niobium, or an alloy thereof, and it is more preferable that the metal is pure titanium or stainless steel. Particularly, it is preferable that these metals are used alone due to galvanic corrosion to be described later.

The metal powder is a main material of the slurry S. It is preferable that the content of the metal powder is in the range of 30 to 80 mass % in the slurry S. It is more preferable that in a process of preparing the metallic porous thin plate to be described later, the content of the metal powder is in the range of 50 to 80 mass % when the foaming process is not performed, or in the range of 40 to 70 mass % when the foaming process is performed. When the content of the metal powder is set in the above range, a final shape (including a pore diameter, a porosity, a thickness, and the like) of the metallic porous thin plate is easily controlled, and the metal powder can be balanced with another component (foaming agent or the like) in the slurry S or the kind of metal.

It is preferable that an average grain diameter of the metal powder be in the range of 0.5 to 50 µm. Since the average grain diameter is set in the above range, the metallic porous thin plate can easily obtain a desired porosity or average pore diameter. The average grain diameter of the metal powder can be measured by a laser diffractometry or the like.

It is preferable that the metal of the metal powder is the same kind as used for the main body of a medical device. For this reason, the joining strength between the metallic porous thin plate and the main body of a medical device is improved. Further, the galvanic corrosion (elution of metal ions) which is caused when a metal comes in contact with another metal in the living body is controlled, and the corrosion resistance is improved. In case of a conventional metallic porous body prepared by a plating method, it is considered that a surface layer of a metallic porous body may be broken by the galvanic corrosion or a foreign-body reaction (an inflammatory reaction, an immune reaction, or the like) in the living body. The same metal can be used for the metallic porous thin plate and the main body of a medical device, and thus the above-described problems are not caused. As specific examples thereof, a SUS316L porous thin plate can be mentioned in respect to a SUS316L medical device main body, a pure titanium porous thin plate can be mentioned respect to a pure titanium medical device main body, and a Ti-6A1-4V porous thin plate with respect to a Ti-6A1-4V medical device main body.

It is preferable that the slurry S contains the foaming agent. The metallic porous thin plate having a high porosity is easily obtained by the foaming agent contained in the slurry S.

Examples of the foaming agent include a surfactant, a volatile organic solvent, and the like. It is preferable that the foaming agent is a non-water-soluble organic solvent of hydrocarbon with 5 to 8 of carbons, and it is more preferable that the foaming agent is neopentane, hexane, heptane, or cyclohexane. These foaming agents may be used alone, or in combination of two or more kinds.

It is preferable that the slurry S contains a water-soluble resin binder. The metallic porous thin plate has a more excellent skeleton by the water-soluble resin binder contained in the slurry S.

As the water-soluble resin binder, it is preferable to use methylcellulose, hydroxypropyl methylcellulose, polyvinyl butyral, polyvinyl alcohol, or the like. These water-soluble resin binders may be used alone, or in combination of two or more kinds.

Moreover, it is preferable that the slurry S contains water.

If necessary, another component, e.g., the plasticizing agent such as glycerin, ethylene glycol, and polyethyleneglycol; the organic solvent such as methanol, ethanol, and isopropanol, and the like can be used.

When the slurry S (paste) does not contain the foaming agent, commercially available plastic beads such as acrylic, polyethylene, or polystyrene beads, which are used for adjusting the porosity or the average pore diameter and prepared according to respective grain sizes, may be used.

Figure 1A:
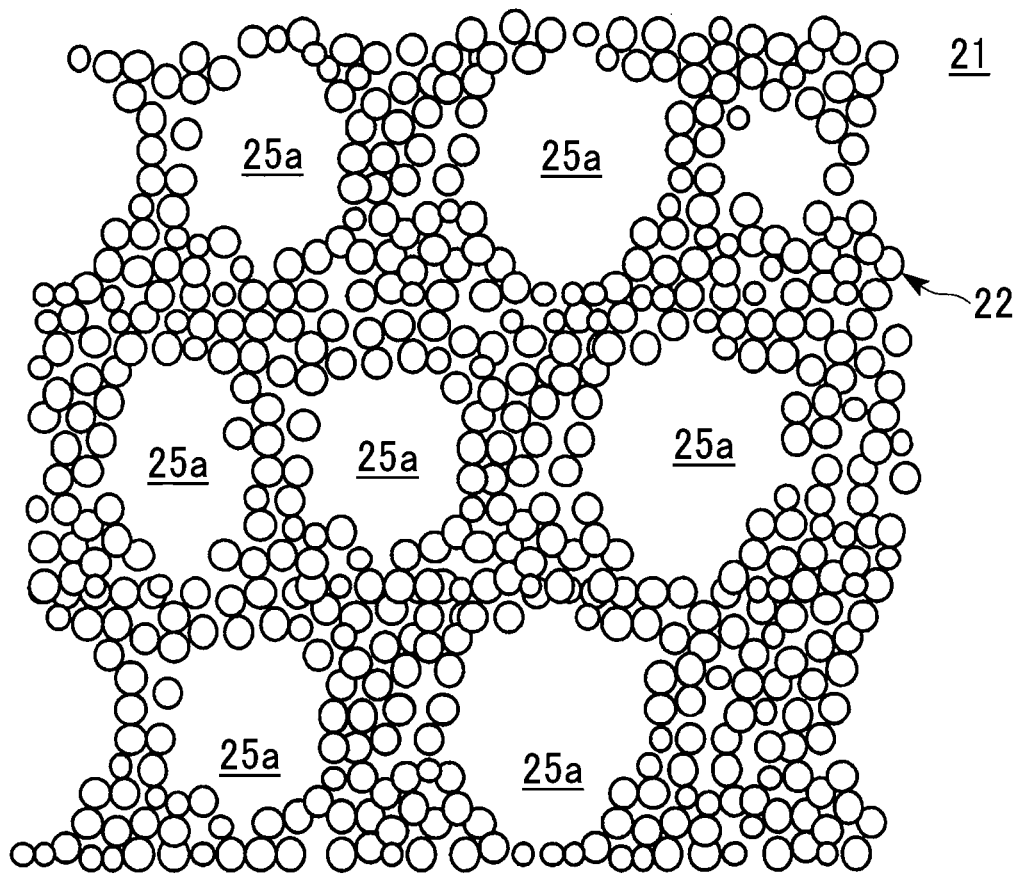
FIG. 1A is an enlarged plan view illustrating an embodiment of a metallic porous thin plate.
Figure 1B:
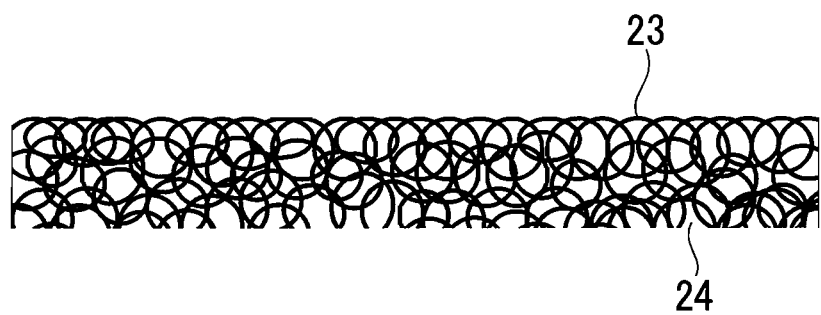
FIG. 1B is a schematic side view illustrating an embodiment of the metallic porous thin plate.

In FIG. 1, an embodiment of the metallic porous thin plate according to the invention is illustrated. FIG. 1A is an enlarged plan view of the metallic porous thin plate, and FIG. 1B is a schematic view illustrating a side of the metallic porous thin plate prepared when the foaming process is performed (the foaming agent is contained in the slurry S).

The metallic porous thin plate illustrated in FIG. 1 has a sheet shape. As illustrated in FIG. 1A, countless numbers of pores 25a, which are opened to front and rear surfaces and side surfaces of the metallic porous thin plate 21, are formed in the metallic porous thin plate.

That is, the metallic porous thin plate has the same pores 25a with each other, which are opened to the front and rear surfaces of the metallic porous thin plate 21, and has the three-dimensional net-like cell structure.

As shown in FIG. 1B, the front and rear surfaces of the metallic porous thin plate 21 includes: a surface 23 (front surface) in which three-dimensionally swollen foamed pores are formed by the foaming process; and a rear surface 24 which comes in contact with a carrier sheet 12.

It is preferable that the thickness of the metallic porous thin plate 21 is in the range of 150 to 2000 μm.

Raw metals to be used for the metallic porous thin plate 21 can be properly selected as described above. The average pore diameter, the porosity, or the like of the metallic porous thin plate 21 can be controlled by adjusting the average grain diameter of the metal powder or the paste composition or controlling the foaming process. Further, for the purpose of accurately controlling the thickness, porosity, or surface flatness of the metallic porous thin plate 21 to a predetermined target value, it is preferable that the metallic porous thin plate 21 after sintering is subjected to a rolling or press process.

It is preferable that the average pore diameter of the metallic porous thin plate according to the invention is in the range of 20 to 800 μm, and it is more preferable that the average pore diameter of the metallic porous thin plate be in the range of 100 to 600 μm. Since the average pore diameter of the metallic porous thin plate is equal to or more than a lower limit of the above range, the pores have the size suitable to the penetration and proliferation of the living tissue, and the penetration rate and proliferation rate of the cells are improved. Since the average pore diameter of the metallic porous thin plate is equal to or less than an upper limit of the above range, a more excellent positional relation (interval) between the skeletons, which is a cell-proliferation region, is made, and the penetration rate and the proliferation rate of the cells are improved.

The average pore diameter of the metallic porous thin plate is measured by direct observation using an optical microscope or an electronic microscope, a bubble point method, a mercury porosimeter method, or the like.

It is preferable that a specific surface area of the metallic porous thin plate according to the invention is in the range of 0.01 to 0.5 $m^2/g$, and it is more preferable that the specific surface area of the metallic porous thin plate is in the range of 0.02 to 0.2 $m^2/g$. As for the specific surface area, a surface area in which the cells can be implanted and proliferated increases with an increase of the specific surface area. When the specific surface area of the metallic porous thin plate is more than 0.5 $m^2/g$, the implantation and proliferation of the cells are affected.

The specific surface area of the metallic porous thin plate is measured by a gas adsorption/desorption method (a BET method) using a krypton gas, a nitrogen gas, or the like.

It is preferable that the porosity of the metallic porous thin plate according to the invention is in the range of 40 to 97%, and it is more preferable that the porosity of the metallic porous thin plate is in the range of 50 to 95%. Since the porosity is less than 40%, a volume of a pore portion of the porous structure is reduced, and the penetration and proliferation rates of the cells from the living tissue are reduced. Since the porosity is more than 97%, a skeleton portion of the metallic porous thin plate is reduced, and the strength of the metallic porous thin plate or the joining strength between the metallic porous thin plate and the main body of a medical device is reduced.

In this specification and claims, 'porosity' means a ratio of pores (corresponding to reference numeral 25a illustrated in FIG. 1A) to the volume of the whole metallic porous thin plate (single layer).

The porosity of the metallic porous thin plate is calculated from the weight ($g/cm^2$), the thin plate thickness, and the theoretical specific gravities of components.

Generally, as for a metallic sintered body, a strength is improved since a metal portion increases with reduction of a porosity, and a joining strength when it is joined to another metal is also improved. However, the strength is reduced with an increase of the porosity, and the joining strength when it is joined to another metal is also reduced.

In the case of a general metal powder compact prepared without the slurry molding, the joining strength between adjacent metal powder grains is low when a porosity is equal to or more than 50%. Further, the general metal powder compact hardly exists as an independent compact when the porosity is equal to or more than 70%.

However, the metallic porous thin plate used in the invention has high porosity and high strength, as described above. It is believed that the reason is that as for the metallic porous thin plate, the metallic skeleton having a solid structure is formed by continuous metal powder sintering on the surface of the pores 25a, as illustrated in FIG. 1. Accordingly, this metallic porous thin plate has high strength and excellent deformability. As a result, the metallic porous thin plate can be strongly joined, since the metallic porous thin plate is easily deformed to follow the surface shape of the main body of a medical device and the adhesion of the metallic porous thin plate to the main body of a medical device increases. In addition, when the medical device to which this metallic porous thin plate is joined is implanted into the body and deformed by a load, the metallic porous thin plate can be also easily deformed, and thus the metallic porous thin plate is prevented from being peeled off from the main body of a medical device. This advantage can be achieved even when the metallic porous thin plate is multilayered.

The metallic porous body according to the invention is formed in multilayers. For example, the metallic porous body is obtained by properly combining the metallic sintered body molded into a sheet shape, the metallic porous thin plate prepared when the foaming process is performed (the foaming agent is contained in the slurry S), and the metallic porous thin plate prepared when the foaming process is not performed (the foaming agent is not contained in the slurry S), thereby forming them into multilayers. It is preferable that the metallic porous body includes the metallic porous thin plate prepared when the foaming process is performed (the foaming agent is contained in the slurry S) among them. Specifically, it is preferable that the metallic porous body is a metallic porous body in which the metallic porous thin plate prepared when the foaming process is performed (the foaming agent is contained in the slurry S) is multilayered or a metallic porous body in which the metallic porous thin plate prepared when the foaming process is not performed and the metallic porous thin plate prepared when the foaming process is performed are formed into multilayers. In addition, it is more preferable that the metallic porous body is a metallic porous body in which a plurality of the metallic porous thin plates having different porosities are formed into multilayers. Since the metallic porous body is formed in multilayers, characteristics (porosity and the like) of the surfaces of be metallic porous body on the main body of a medical device side and on the living tissue side can be easily controlled.

Here, as for the metallic porous body, it is preferable that the porosity of the metallic porous thin plate joined to side of the main body of a medical device is lower than the porosity of the metallic porous thin plate coming in contact with the living tissue.

It is preferable that the metallic porous thin plate having a low porosity is used as a joining surface to the main body of a medical device in order to increase the joining strength between the metallic porous body and the main body of a medical device. In addition, it is preferable that the metallic porous thin plate having a high porosity is used as a contacting surface with the living tissue in order to control the penetration of the cells from the living tissue or the living tissue structure. Accordingly, as described above, by controlling the porosity of the metallic porous body when being formed in multilayers, the medical device surface modification member, which is excellent in penetration property of the cells from the living tissue or in control (connectivity between the medical device and the living tissue) of the structure of the living tissue formed around the metallic porous body, and in which the hard-to-peel metallic porous body is strongly joined to the main body of a medical device, can be obtained.

Figure 2:
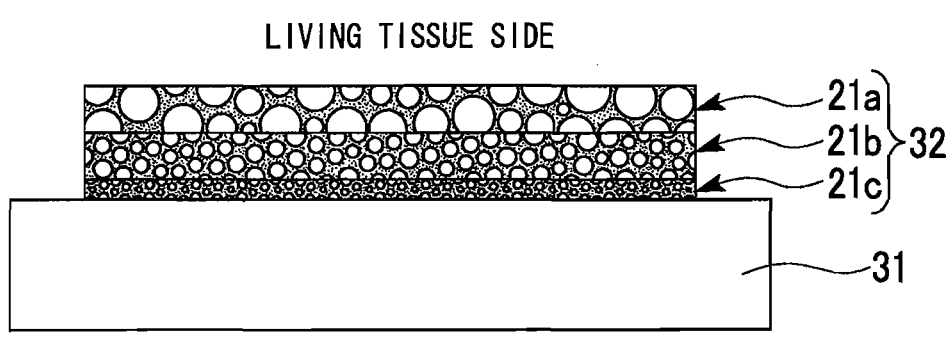
FIG. 2 is a cross-sectional view illustrating an embodiment of a metallic porous body formed in multilayers.

An embodiment of the metallic porous body in which the metallic porous thin plate is multilayered is illustrated in FIG. 2.

In FIG. 2, a metallic porous body 32 which includes metallic porous thin plates 21a, 21b, and 21c having different porosities is joined to a surface of a surface of the main body of a medical device 31.

Further, in FIG. 2, the porosities of the metallic porous thin plates 21a, 21b, and 21c become higher in a thickness direction from the main body of a medical device 31 to the living tissue, that is, in an order of the metallic porous thin plate 21c, the metallic porous thin plate 21b, and the metallic porous thin plate 21a.

As for the metallic porous body, it is preferable that the average pore diameter of the metallic porous thin plate joined to the main body of a medical device be in the range of 20 to 150 μm, and it is preferable that the average pore diameter of the metallic porous thin plate coming in contact with the living tissue be in the range of 100 to 600 μm.

It is preferable that the porosity of the metallic porous thin plate joined to the main body of a medical device is in the range of 50 to 85%, and it is preferable that the porosity of the metallic porous thin plate coming in contact with the living tissue be in the range of 80 to 95%.

'Contacting surface with living tissue' is a frontmost surface of the metallic porous thin plate on the living tissue side.

A surface of the skeleton including a sintered body of the metal powder of the metallic porous thin plate may be covered with an inorganic compound having biocompatibility.

Accordingly, compatibilities of the metallic porous thin plate and the metallic porous body in which the metallic porous thin plate is multilayered with the living tissue increases, and the penetration rate and the proliferation rate of the cells from the living tissue are improved.

Examples of the inorganic compound having biocompatibility include a metal oxide such as a titanium oxide, calcium phosphate, hydroxyapatite, and the like. These inorganic compounds having biocompatibility may be used alone, or in combination of two or more kinds.

As a covering method, a physical covering method such as applying or spraying of a slurry containing a powder of an inorganic compound having biocompatibility, a method with the accompanying chemical reaction such as a precipitation method from an aqueous solution or Chemical Vapor Deposition (CVD), or the like can be properly selected.

The covering by the inorganic compound may be performed before or after the metallic porous body is joined to the surface of the main body of a medical device. There are some cases in which the inorganic compound needs to be baked when it covers the surface of the skeleton including the sintered body of the metal powder of the metallic porous thin plate (in case of the chemical precipitation method). Here, when a temperature for baking of the inorganic compound is lower than a joining temperature, and after the baking, there is concern that improvements in the compatibility with the living tissue may be damaged by heating, it is preferable that the covering is performed after the joining.

By the inorganic compound having biocompatibility, the whole or a part of the surface of the skeleton of the metallic porous thin plate may be covered.

The metallic porous body, or a part of the metallic porous thin plates constituting the metallic porous body may contain a drug in their pores by controlling the pores. If necessary, the porous surface may be covered with a biodegradable polymer such as polylactate. Accordingly, by slowly emitting the drug from the medical device surface after implantation into the body, medical treatment for diseases or recovering of the living tissue around the medical device can be facilitated. In addition, by injecting the cells preliminarily sowed and cultured outside the body into the metallic porous body or a part of the metallic porous thin plates constituting the metallic porous body, regeneration of the living tissue around the medical device after implantation into the body or medical treatment for diseases can be facilitated.

It is preferable that the metallic porous body be constituted by the above-described metallic porous thin plate. However, a known medical device surface modification member also can be used without being limited by this.

<Surface Modification Method for Medical Device>

The surface modification method for a medical device according to the invention is a method of: preparing the metallic porous thin plate by molding the slurry containing the metal powder and the foaming agent into a sheet shape, subjecting the slurry to the foaming process, drying the slurry, and defatting and sintering the resulting compact; preparing the metallic porous body by employing the multilayered metallic porous thin plate; deforming the metallic porous body to match at least a part of the surface shape of the main body of a medical device and joining it; and deforming the metallic porous thin plate to match and join at least a part of the surface shape of the main body of a medical device.

It is preferable that the metallic porous thin plate includes a metallic porous thin plate prepared by molding the slurry containing the metal powder and the foaming agent into a sheet shape, subjecting the slurry to the foaming process, drying the slurry, and defatting and sintering the resulting compact.

Further, it is preferable that the slurry be molded into a sheet shape by the doctor blade method in the surface modification method for a medical device according to the invention. In addition, it is preferable that the joining is diffusion joining.

Hereinafter, a process of preparing the metallic porous thin plate and a process of joining the metallic porous thin plate to the main body of a medical device will be described in detail with specific examples.

<Process of Preparing Metallic Porous Body>

In this process, the metallic porous thin plate is prepared by molding the slurry S into a sheet shape, drying the slurry S, and defatting and sintering the resulting compact, and the metallic porous body is prepared by employing the multilayered metallic porous thin plate.

It is preferable that the metallic porous thin plate includes a metallic porous thin plate prepared by molding the slurry S containing the metal powder and the foaming agent into a sheet shape, subjecting the slurry S to the foaming process, drying the slurry S, and defatting and sintering the resulting compact.

It is preferable that the slurry S be molded into a sheet shape by the doctor blade method.

Hereinafter, this process will be described with reference to the drawings.

Figure 3:
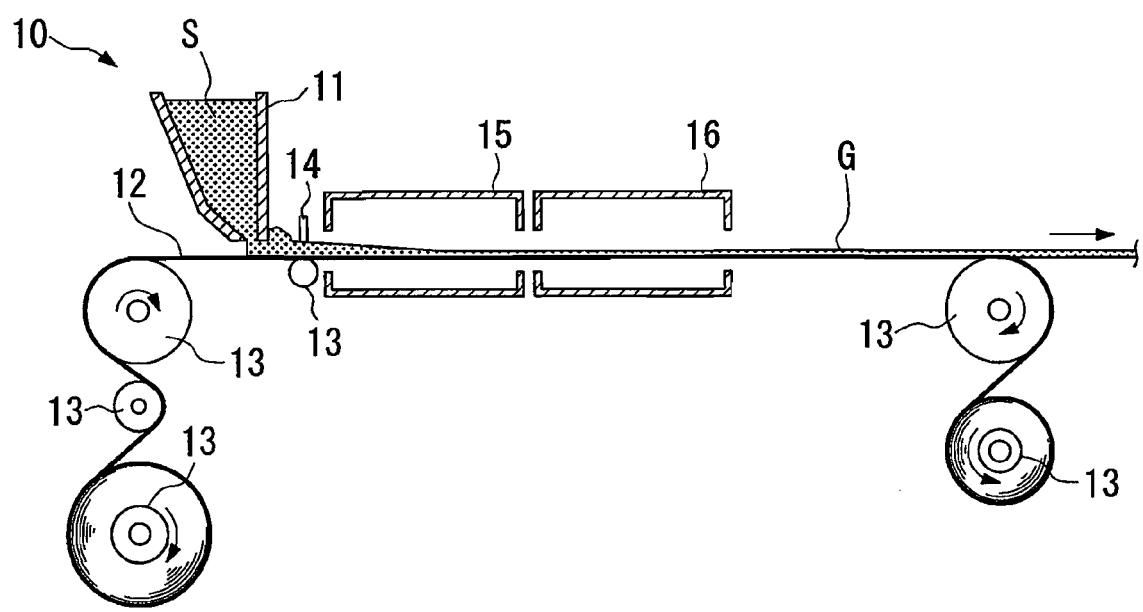
FIG. 3 is a schematic view illustrating an example of a method of preparing a metallic porous thin plate.

In FIG. 3, an example of the method of preparing the metallic porous thin plate is illustrated. In this figure, an example, in which the doctor blade method is used and the foaming process is performed, is illustrated.

The slurry S is a slurry containing at least the metal powder. It is preferable that the slurry S contains the foaming agent, water-soluble resin binder, and water, and if necessary, another component such as the plasticizing agent or organic solvent.

The slurry S is molded into a sheet shape. The molding method is not particularly limited if the slurry S can be molded in a desired sheet shape. It is, however, particularly preferable that the doctor blade method be used. For example, by using a green sheet preparing apparatus 10 illustrated in FIG. 3, the slurry S can be molded in a thin sheet shape.

In the green sheet preparing apparatus 10, firstly, the slurry S is supplied onto the carrier sheet 12 from a hopper 11 storing the slurry S. The carrier sheet 12 is conveyed by rollers 13. The slurry S on the carrier sheet 12 is extended between the moving carrier sheet 12 and a doctor blade 14, and is molded so as to have a desired thickness.

It is preferable that the gap between the carrier sheet 12 and the doctor blade 14 be in the range of 100 to 1500 μm.

Here, the molding by the doctor blade method may be performed more than once in order to obtain the multilayered metallic porous thin plate (metallic porous body). As this method, for example, a method illustrated in FIG. 4 can be employed.

Figure 4:
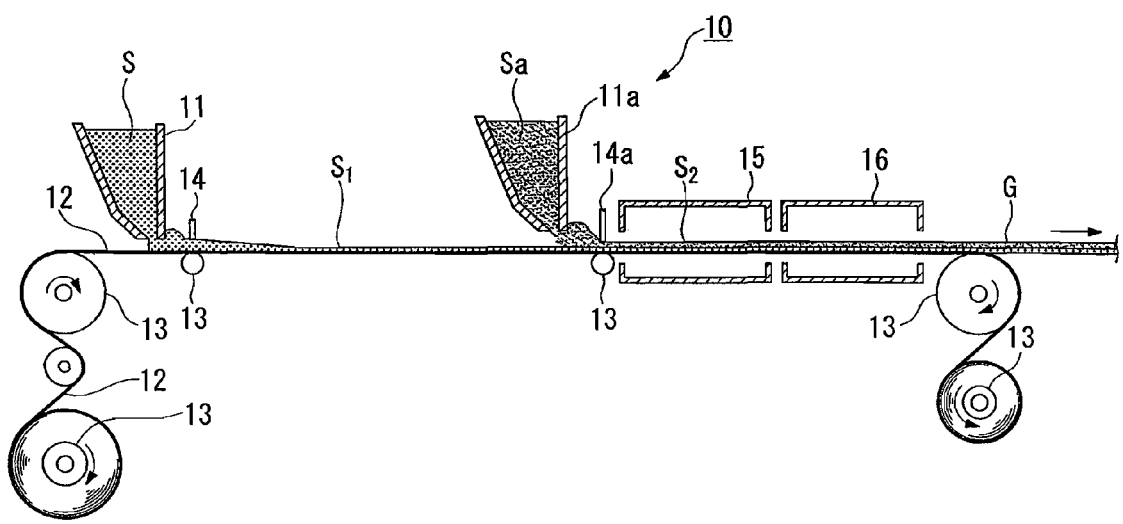
FIG. 4 is a schematic view illustrating an example of a method of forming a metallic porous body including two layers of metallic porous thin plates.

FIG. 4 is a view illustrating an example of a method of molding the metallic porous body including two metallic porous thin plates.

In the green sheet preparing apparatus 10, firstly, the slurry S is supplied onto the carrier sheet 12 from the hopper 11 storing the slurry S. The slurry S is extended between the moving carrier sheet 12 and the doctor blade 14, and thus a first slurry layer S1 is molded.

Next, a slurry Sa having a different combination ratio is supplied onto the first slurry layer S1 from a hopper 11a. By a doctor blade 14a, a second slurry layer S2 having a specified thickness is molded on the first slurry layer S1.

When three or more layers of metallic porous thin plates are formed, the molding is performed in an order that a third slurry layer S3 is molded on the second slurry layer S2 and a fourth slurry layer S4 is molded on the third slurry layer S3. Accordingly, the porosity, the average pore diameter, or the like is controlled in a thickness direction, and the metallic porous body having two frontmost surfaces, each having a different porosity or a different average pore diameter, can be prepared.

Next, the molded slurry S is conveyed by the carrier sheet 12 and is subjected to heating. In FIG. 3, the slurry S sequentially passes through a foaming tank 15 and a heating furnace 16.

In the foaming tank 15, by controlling a temperature condition under a high-temperature atmosphere with a humidity of 80% or more, a pore diameter of countless numbers of foamed pores formed by action of the foaming agent is uniformly controlled over the whole slurry S, and the three-dimensional net-like skeleton (the skeleton of the metallic porous thin plate) constituted from the slurry components containing the metal powder is formed.

At this time, the foamed pores are flatly formed on the contacting surface (rear surface) of the slurry S with the carrier sheet 12. In addition, the pores, which are three-dimensionally swollen by free foaming, are formed on the opposite surface (front surface) to the contacting surface of the slurry S with the carrier sheet 12. Therefore, the front and rear surfaces have a foamed structure in which they are asymmetric with respect to each other.

It is preferable that the surface shape of the joining surface between the metallic porous thin plate and the main body of a medical device be asymmetric with respect to the surface shape of the contacting surface between the metallic porous thin plate and the living tissue.

Since the front and rear surfaces of the metallic porous thin plate are asymmetric with respect to each other, the characteristics of the surfaces are easily controlled so as to be suitable to the joining strength of the main body of a medical device and the penetration and proliferation of the living tissue. For example, one embodiment thereof is the metallic porous thin plate 21 having: the front surface 23 in which the three-dimensionally swollen foamed pores are formed as illustrated in FIG. 1B; and the rear surface 24 in which the flat foamed pores are formed and which comes in contact with the carrier sheet 12.

Next, by drying the foamed body formed on the carrier sheet 12 in the air or in an inert gas atmosphere at a temperature of 100° C. or lower in the heating furnace 16, a resulting compact (hereinafter, may be referred to as 'green sheet G') is formed.

By peeling off the green sheet G from the carrier sheet 12 and holding it for about 1 to 10 hours at a temperature in the range of 350 to 600° C.; performing the decomposition of the components other than the metal powder contained in the slurry S and the defatting, while the foamed pore structure is maintained; and holding the resulting porous metallic defatted body formed from the skeleton in which the metal powder is concentrated for about 1 to 10 hours at a temperature in the range of 1100 to 1350° C., a metallic porous sintered sheet in which the metal powder is sintered is obtained. By cutting the obtained metallic porous sintered sheet to a predetermined size, the metallic porous thin plate is prepared.

By preliminarily preparing a plurality of the metallic porous thin plates and forming them into multilayers by the joining or the like, the metallic porous body is prepared.

According to the invention, the forming of the metallic porous thin plates into multilayers may be carried out by, for example: the lamination of the preliminarily prepared metallic porous thin plates; the molding once or more by the doctor blade method; or the overlapping of a plurality of the metallic porous thin plates on the main body of a medical device in a process to be described later and joining them to each other by a one-time process. For example, when the metallic porous thin plate which does not need the foaming process and the metallic porous thin plate which needs the foaming process are formed into multilayers, it is preferable to employ a method of: firstly molding the metallic porous thin plate which does not need the foaming process by the doctor blade method; secondarily molding the metallic porous thin plate which needs the foaming process by the doctor blade method;

and laminating both of them, from the viewpoint of the height of the joining strength between both of them and simplification of the preparing process.

According to the invention, the doctor blade method is not essential. However, it is preferable to use the doctor blade method since the thin-plate shape suitable to the medical device surface modification member can be easily molded.

The foaming process is also not essential. However, it is preferable to perform the foaming process since the porosity or the average pore diameter is easily controlled, or since the metallic porous thin plate having the high porosity and the high strength is easily obtained. Particularly, it is preferable that the metallic porous thin plate constituting the contacting surface of the metallic porous body with the living tissue be molded through the foaming process.

<Process of Joining Metallic Porous Body to Medical Device Main Body>

In this process, the metallic porous body prepared by the above-described process is deformed to follow at least a part of the main body of a medical device and joined. It is preferable that the joining be the diffusion joining. By this, the characteristics of the surface of the main body of a medical device are varied.

Hereinafter, this process will be described in detail.

The metallic porous body prepared by the above-described process is cut to be fitted to the shape of the surface which is a joining target portion of the main body of a medical device.

As a cutting method, a general piece cutting method, such as knife cutting performed by a cutter or the like, laser cutting, a waterjet process, discharge wire cutting, or ultrasonic cutting, can be used.

Next, the metallic porous body cut in a predetermined shape is adhered to a surface of the joining target portion of the main body of a medical device, and is subjected to plastic deformation so as to be fitted to the shape of the surface.

Then, the metallic porous body is joined to the main body of a medical device and formed integrally therewith.

Figure 5:
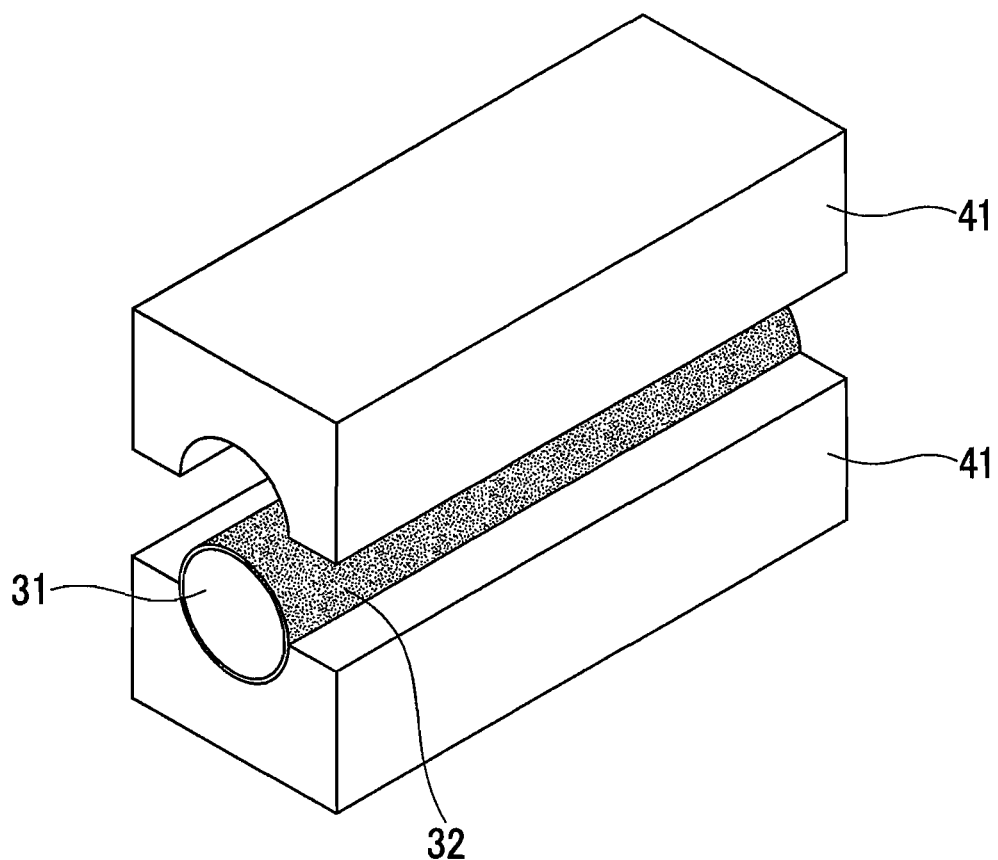
FIG. 5 is a schematic view illustrating a 'mold' for joining the metallic porous body to the main body of a medical device.

Here, in order to improve the adhesion between the metallic porous body 32 and the surface of the main body of a medical device 31, it is preferable to use 'mold' 41 fitted to the surface shape of the joining target portion as illustrated in FIG. 5.

As the joining method, it is preferable to employ the diffusion joining in which the mold 41, to which the main body of a medical device 31 and the metallic porous body 32 are fixed by applying a pressure, are heated and held in vacuum or in a non-oxidizing atmosphere of an inert gas or the like, from the viewpoint of the joining strength between the main body of a medical device 31 and the metallic porous body 32. Here, in order to secure the joining strength between them, it is preferable that a pressure of 0.01 to 10 MPa is applied to the joining surface. Since the pressure to be applied is equal to or more than a lower limit of the range, more excellent joining strength is obtained. Moreover, since the pressure to be applied is equal to or less than an upper limit of the range, unnecessary deformation of the metallic porous body 32 can be suppressed, and a desired thickness is easily obtained.

Using the deformation during the joining, a method of performing pressing and heating by using a joining mold having a gap fitted to the desired thickness can be used. In this case, it is preferable that a pressure of 0.1 to 10 MPa is applied to the joining surface. It is preferable that an optimum value of the pressure is properly selected by the material and porosity of the metallic porous body 32, the surface treatment method (shape, treatment temperature, need for plastic deformation), and the like.

The use of the mold 41 is effective for preventing foreign particles from being mixed at the time of joining.

Further, according to requirements such as a joining shape, spot or seam welding using, e.g., laser, resistance heating, an ultrasonic waver, or the like, a blazing method, or the like also can be properly applied as the joining method as well as the diffusion joining.

When several kinds of the metallic porous thin plates are joined to the main body of a medical device 31, the metallic porous body 32 in which the metallic porous thin plates are preliminarily linked with a certain characteristics (i.e. pore diameter distribution) and formed into multilayers can be joined to the main body of a medical device 31 by using the method illustrated in FIG. 5. Particularly, it is preferable to use the method in case of a complicated shape.

In addition, a plurality of the metallic porous thin plates overlapped on the main body of a medical device 31 can be joined to each other by a one-time process.

As specific conditions of the joining between the main body of a medical device 31 and the metallic porous body 32, the material of the mold 41 may be graphite, aluminum, zirconia, silica, high-purity quartz, boron nitride, or the like. It is preferable to use graphite due to excellent processability, or high-purity quartz due to excellent cleanliness.

When graphite is used for the mold, there are some cases in which graphite reacts with the metal of the joining target. Accordingly, if necessary, a barrier layer may be provided on a portion coming in contact with the metallic porous body 32. For example, as the barrier layer, it is preferable to use a sprayed layer of a ceramic member such as zirconia, aluminum, or the like.

It is preferable that vacuum is equal to or less than $5.0 \times 10^{-2}$ Pa. An Ar atmosphere also can be employed.

As for a period of time for joining, it is preferable that the holding be performed for about 1 to 5 hours at a predetermined temperature.

It is preferable that the joining method be the diffusion joining. Since the joining method is the diffusion joining, a higher joining strength can be obtained.

It is preferable that a joining temperature be in the range of 700 to 1200° C., and it is more preferable that the joining temperature be in the range of 800 to 100° C. Since the joining temperature is equal to or more than 700° C., a more preferable joining strength can be obtained. Since the joining temperature is equal to or less than 1200° C., the sintering of the metallic porous body 32 is suppressed, and thus a desired porosity can be stably obtained. In addition, a thermal effect on the main body of a medical device 31 can be kept at a low level, and thus the mechanical characteristics are improved. Moreover, it is preferable that an optimum joining temperature be properly selected based on the materials, porosities, and the like of the metallic porous thin plate and the metallic porous body 32 in which the metallic porous thin plate is multilayered.

The metallic porous body 32 is joined to at least a part of the surface of the main body of a medical device 31. The metallic porous body may be joined to the whole or a part of the surface of the main body of a medical device 31 for different purposes.

The metallic porous body is low in deformation resistance as compared with a general bulk metal material. Since the joining between the metallic porous body and the main body of a medical device is substantially performed in the skeleton portion present in a part of the contacting surface, and the joining area is small, the joining can be performed at low stress or at a low temperature when compared with a bulk metal material having the same shape.

Accordingly, even when the surface of the main body of a medical device has a high curvature, the metallic porous body can be preliminarily deformed to follow the surface shape of the main body of a medical device and joined to the main body of a medical device.

<Surface Modification Method for Medical Device>

The surface modification method for a medical device according to this aspect is a method of: preparing the metallic porous thin plate by molding the slurry containing the metal powder into a sheet shape, drying the slurry, and defatting and sintering the resulting compact; preparing the metallic porous body by employing the multilayered metallic porous thin plate; and deforming the metallic porous body to follow at least a part of the surface shape of the main body of a medical device and joining it. It is preferable that the metallic porous thin plate includes a metallic porous thin plate prepared by molding the slurry containing the metal powder and the foaming agent into a sheet shape, subjecting the slurry to the foaming process, drying the slurry, and defatting and sintering the resulting compact.

It is preferable that the slurry is molded into a sheet shape by the doctor blade method in the surface modification method for a medical device according to this aspect. In addition, it is preferable that the joining is the diffusion joining.

Treatment methods are the same as in the above-described medical device preparing method, and a description thereof will be omitted.

According to this aspect, by joining the metallic porous body in which the metallic porous thin plate as the medical device surface modification member having the excellent connectivity with the living tissue to the surface of the main body of a medical device with the high joining strength, the surface modification method for a medical device by which the metallic porous body can be easily joined to the surface of the main body of a medical device having various surface shapes can be provided.

As compared with a conventional medical device, the medical device provided according to this aspect is has better in joining strength than the main body of a medical device, and can be prepared inexpensively.

Further, by the surface modification method for a medical device according to this aspect, the medical device having the high porosity can be provided.

Further, by the surface modification method for a medical device according to this aspect, the metallic porous body as the medical device surface modification member can be easily joined to a known medical device main body having various surface shapes.

It is preferable that the porosity of the metallic porous thin plate prepared according to this aspect be in the range of 50 to 97%, it is more preferable that the porosity of the metallic porous thin plate be in the range of 60 to 97%, and it is even more preferable that the porosity of the metallic porous thin plate be in the range of 70 to 90%. When the porosity is less than 50%, the volume of the pore portion of the porous structure is reduced, and the penetration and proliferation rates of the cells from the living tissue are reduced. When the porosity is more than 97%, the skeleton portion of the metallic porous thin plate is reduced, and the strength of the metallic porous thin plate or the joining strength between the metallic porous thin plate and the main body of a medical device is reduced.

EXAMPLES

Hereinafter, the invention will be described in detail with Examples. However, the invention is not limited to these Examples.

A joining strength evaluation was performed on joining specimens (Example 1) according to the invention, to which a metallic porous body including a multilayered metallic porous thin plate was joined.

In addition, a living tissue connectivity evaluation was performed on multilayer-joining bodies (Examples 2 and 3) according to the invention, to which a metallic porous body including a multilayered metallic porous thin plate was joined.

[Joining Strength Evaluation]

The joining strength evaluation was performed on the joining specimens (Example 1) according to the invention, to which the metallic porous body including the multilayered metallic porous thin plate was joined.

For Test Examples, the same joining strength evaluation (Test Examples 1 and 2) as in Example 1 was performed on the joining specimens to which the metallic porous thin plate (single layer) used in the invention was joined. In addition, for comparative tests with respect to Test Examples 1 and 2, a comparative evaluation (Test Examples 3 and 4) was performed using the same metallic porous thin plate as a substance.

Test Example 1

Figure 7A:
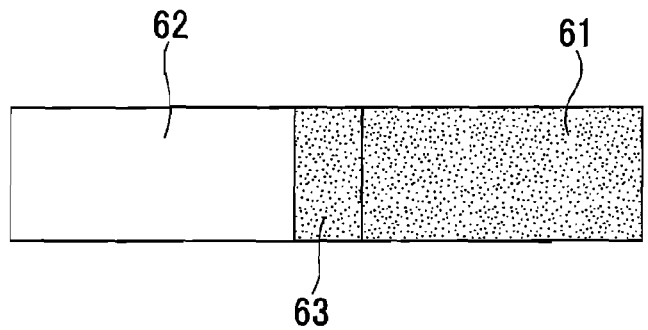
FIG. 7A is a plan view of a joining specimen, illustrating a method of evaluating a joining strength.

SUS316L porous thin plates 61 (average pore diameter of 150 μm, porosity of 87%, thickness of 0.31 mm) which were cut to a size of 20 mm×50 mm and had a three-dimensionally-open pore structure and SUS316L foil members 62 (thickness of 0.5 mm) were overlapped each other by 10 mm to be fixed, as shown in FIG. 7A. They were subjected to diffusion joining by being heated to 1050° C. in an Ar atmosphere while bonded and pressed at 1.5 MPa. As a result, five joining specimens having a size of a width 20 mm×a length 90 mm were prepared.

Using a universal tester Autograph (manufactured by Shimadzu Corporation, load cell capacity: 5 kN), the five joining specimens prepared as described above were fixed at both ends thereof by 10 mm, respectively, and a tensile test was performed on the joining specimens at a tensile rate of 1.5 mm/min.

The tensile test was performed until the joining specimens were broken, and the evaluation was performed about a process of breaking and an area in which the breaking occurred. An average tensile strength at which the breaking of the joining specimens was started was 7.4 MPa.

Test Example 2

Joining specimens were prepared and evaluated in the same manner as in Test Example 1, except that pure Ti porous thin plates (average pore diameter of 50 μm, porosity of 79%, thickness of 0.30 mm) and pure Ti foil members (thickness of 0.5 mm) were used, and they were subjected to the diffusion joining by being heated to 950° C. in vacuum while bonded and pressed at 2.0 MPa. An average tensile strength at which the breaking of the joining specimens was started 12.4 MPa.

Example 1

SUS316 porous thin plates A (average pore diameter of 300 μm, porosity of 89.5%, thickness of 0.42 mm) which were cut to a size of 20 mm×50 mm and had a three-dimensionally-open pore structure and SUS316L foil members (thickness of 0.1 mm) overlapped each other by 10 mm, as shown in FIG. 7A. They were subjected to diffusion joining by being heated to 1050° C. in vacuum while bonded and pressed at 1.5 MPa.

As a result, five joining specimens A having a width of 20 mm×a length of 90 mm were prepared.

Next, the SUS316 porous thin plates A which were cut to a size of 120 mm×70 mm and SUS316L porous thin plates B which had a three-dimensionally-open pore structure (average pore diameter of 50 µm, porosity of 65.3%, thickness of 0.27 mm) were laminated to be completely overlapped with each other. They were subjected to the diffusion joining by being heated to 1050° C. in vacuum while bonded and pressed at 1.5 MPa. As a result, metallic porous bodies C were prepared.

From these metallic porous bodies C (thickness of 0.66 mm), 5 samples having a width of 20 mm and a length of 50 mm were cut. The cut metallic porous bodies C, and SUS316L foil members (thickness of 0.1 mm) which were cut to the same size of a width 20 mm and a length 50 mm as the cut metallic porous bodies were joined as the joining specimens A. As a result, 5 joining specimens B were prepared.

On a SUS316 porous thin plate D-1 as a first layer (average pore diameter of 30 µm, porosity of about 53%, thickness of about 0.15 mm) which was prepared by using a slurry not containing a foaming agent (paste), a SUS316L porous thin plate D-2 as a second layer (average pore diameter of 300 µm, porosity of about 85%, thickness of about 0.3 mm) which was prepared by using a slurry containing the foaming agent (paste) and subjecting the slurry to a foaming process was laminate-molded by a multiple-molding process as illustrated in FIG. 4. A metallic porous sheet E (thickness of 0.45 mm) was prepared by drying, defatting, and sintering the multilayered sheet. From the obtained metallic porous sheet E, samples having a width 20 mm and a length of 50 mm were cut. The cut metallic porous sheets E and SUS316L foil members (thickness of 0.1 mm) which were cut to the same size of a width 20 mm and a length 50 mm as the cut metallic porous sheets were joined as the joining specimens A. As a result, 5 joining specimens C were prepared.

The tensile test evaluation was performed on the obtained joining specimens A, B, and C as in Test Example 1, respectively. The average tensile strength at which the breaking of the joining specimens A was started was 6.5 MPa. The average tensile strength at which the breaking of the joining specimens B was started was 13.6 MPa. An average tensile strength at which the breaking of the joining specimens C was started was 20.8 MPa.

Test Example 3

Specimens were prepared by cutting a SUS316L porous thin plate (average pore diameter of 150 µm, porosity of 87%, thickness of 0.31 mm) to 5 pieces having a size of a width 20 mm×a length 90 mm, and then evaluated as in Test Example 1. The average tensile strength at which the breaking of the porous thin plates of SUS316L was started was 7.5 MPa.

Test Example 4

Specimens were prepared by cutting a pure Ti porous thin plate (average pore diameter of 50 µm, porosity of 79%, thickness of 0.30 mm) to 5 pieces having a width 20 mm and a length 90 mm, and then evaluated as in Test Example 1. An average tensile strength at which the breaking of the pure Ti porous thin plates was started was 12.6 MPa.

Results of Joining Strength Evaluation

Test Examples 1 to 4

In any tensile test of Test Examples 1 to 4, specimen breaking proceeded from a crack formed on one portion of each specimen after yielding.

Figure 7B:
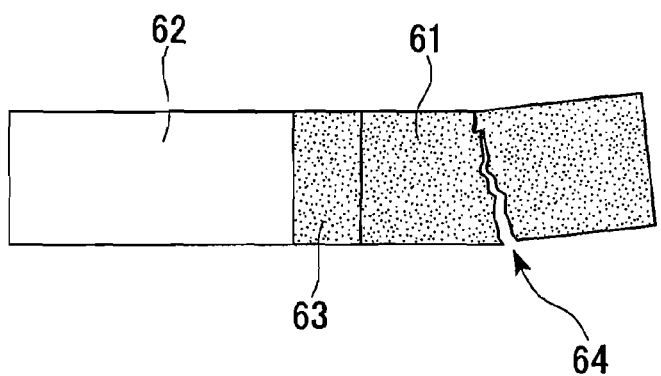
FIG. 7B is a plan view of a state that the joining specimen is broken after a tensile test, illustrating the method of evaluating a joining strength

Further, as shown in FIG. 7B, a breaking portion 64 was located on the side of a metallic porous thin plate 61 with reference to a joining portion 63 in each joining specimens of Test Examples 1 and 2. In addition, peeling was not caused between the metallic porous thin plate 61 and the foil member 62.

As for the tensile strengths at which the breaking of the specimens was started, it was confirmed that a difference between the average tensile strength of the joining specimens of Test Examples 1 and 2 and the average tensile strength of the metallic porous thin plates of Test Examples 3 and 4 was at most about 5% and the specimens have the almost same strength.

From the above-described results, it was confirmed that each metallic porous thin plate 61 used in the invention could be easily joined along a surface shape of each foil member 62. Further, it was confirmed that the strength of the joining portion between each metallic porous thin plate 61 and each foil member 62 was higher than that of the metallic porous thin plate 61 and the diffusion joining provides the sufficient strength.

Example 1

In Example 1, in any joining specimen, the breaking portion 64 was not located in the joining portion 63 but located in the metallic porous thin plate (metallic porous body).

A cross-section of each breaking portion 64 of the joining specimens B and the joining specimens C was observed. Visible peeling was not observed in any joining surface between the metallic porous thin plates (lamination).

From the above-described results, it was confirmed that the material strength of the metallic porous bodies C or the metallic porous sheets E in which the metallic porous thin plate having a lower porosity was multilayered was higher than that of the metallic porous thin plate A as a substance having a higher porosity.

It was confirmed that any of the joining strength between the two metallic porous thin plates and the joining strength between the metallic porous thin plate and the metallic foil member was higher than the strength of the metallic porous thin plate as a substance or the strength of the metallic porous body itself.

From the above-described results, it was confirmed that the joining between the metallic porous thin plates was easy and strong. Further, it was confirmed that by forming the metallic porous thin plate having a higher porosity and the metallic porous thin plate having a lower porosity into multilayers, the strength (joining strength between the multilayered metallic porous thin plate and the metallic foil member) could be substantially improved.

[Living Tissue Connectivity Evaluation]

The living tissue connectivity evaluation was performed on the multilayer-joining bodies (Examples 2 and 3) according to the invention, to which the metallic porous body including the multilayered metallic porous thin plate was joined.

For Test Examples, the same living tissue connectivity evaluation (Test Examples 5 to 10) was performed on metallic porous thin plates used in the invention. In the Test Examples, since an evaluation performed on a medical device in which a metallic porous thin plate is joined to a surface of the main body of a medical device and an evaluation performed on the metallic porous thin plate as a substance lead to the same tendency, a simple evaluation was performed on the metallic porous thin plate as a substance.

A medium prepared by adding a 10 weight % fetal bovine serum (FBS) to a Dulbecco's Modified Eagle Medium (D-MEM) was used as a tissue culture medium.

Test Example 5

A pure titanium porous thin plate having a three-dimensionally-open pore structure (average pore diameter of 150 μm, porosity of 89%, thickness of 0.5 mm, angle of 11 mm) was left still in a tissue culture microplate having 12 holes, and about 100,000 of human osteosarcoma-derived cells Saos-2 were sowed in 2 mL of a cell culture medium (D-MEM+10 weight % FBS).

Figure 8:
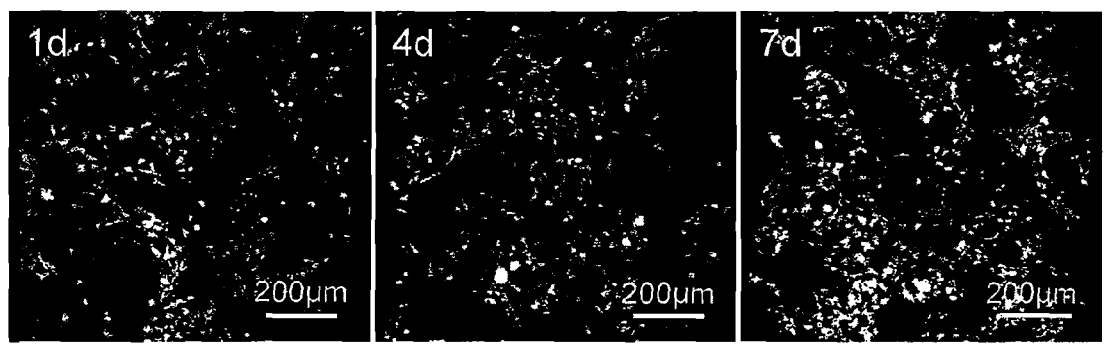
FIG. 8 illustrates images obtained by culturing Saos-2 in a pure titanium porous thin plate and performing fluorescent staining, which are observed by a confocal microscope (Test Example 5)

Next, the cells were cultured for 1, 4, 7 days in an incubator under the environment of 95% air+5% carbon dioxide gas at 37° C., fixed by a 4 volume % formalin buffer solution, and then stained with a fluorescent dye (Texas Red). The cells were observed by a confocal microscope. The evaluation results are illustrated in FIG. 8.

In a confocal microscopic image, a bright portion is a cell. The brighter the image, the more proliferated cells.

Example 2

On a pure titanium porous thin plate 91 having a three-dimensionally-open pore structure (average pore diameter of 600 μm, porosity of 75.3%, thickness of 0.32 mm), another pure titanium porous thin plate 91 having a different pore diameter (average pore diameter of 50 μm, porosity of 79.8%, thickness of 0.30 mm) overlapped, and then a pure titanium foil member (thickness of 0.03 mm) was overlapped thereon. They were subjected to the diffusion joining by being heated to 950° C. in vacuum while being bonded and pressed at 2.0 MPa. A multilayer-joining body to which the above obtained pure titanium porous body was joined was cut at an angle of 11 mm, and then subjected to acetone cleaning and sterilization. In a tissue culture microplate having 12 holes (without cell connectivity process), the cut multilayer-joining body was vertically-installed using a silicon tube 92, as illustrated in FIG. 9, and about 100,000 of human osteosarcoma-derived cells Saos-2 were sowed in 2 mL of a cell culture medium (D-MEM+10 weight % FBS).

Figure 10:
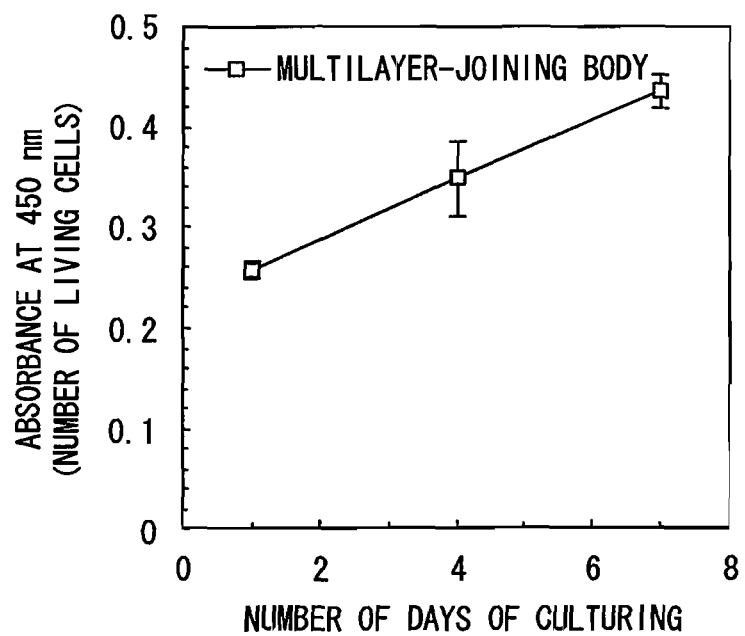
FIG. 10 is a graph illustrating results obtained by culturing Saos-2 in a state that a pure titanium multilayer-joining body is vertically left still and measuring the number of living cells by a WST-1 method (Example 2)

Next, the cells were cultured for 1, 4, 7 days in an incubator under the environment of 95% air+5% carbon dioxide gas at 37° C., and then the number of living cells was measured by a WST-1 method (color development detection method). The evaluation results are illustrated in FIG. 10.

Test Example 6

Figures 9A, 9B:
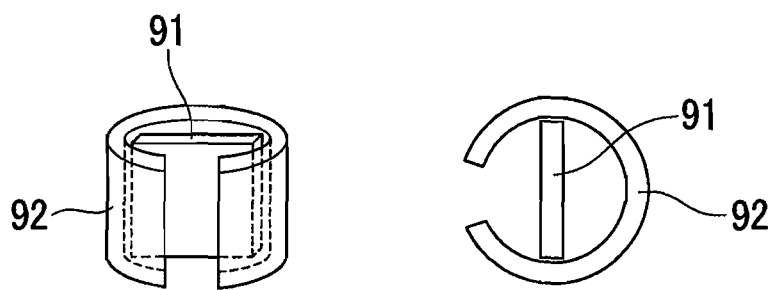
FIG. 9A is a schematic view illustrating a method of vertically-fixing a metallic thin plate by using a silicon tube.
FIG. 9B is a schematic view illustrating the method of vertically-fixing a metallic thin plate by using the silicon tube.

In a tissue culture microplate having 12 holes (without cell connectivity process), 4 SUS316L porous thin plates 91 having a three-dimensionally-open pore structure (average pore diameters of 50, 150, 300, and 600 μm, porosities of 85.3, 84.9, 84.7, and 85.3%, thickness of 0.31, 0.63, 0.43, and 0.46 mm, angle of 11 mm) were vertically-installed using a silicon tube 92, as illustrated in FIG. 9, and about 100,000 of Saos-2 were sowed in 2 mL of a cell culture medium (D-MEM+10 weight % FBS).

Figure 11:
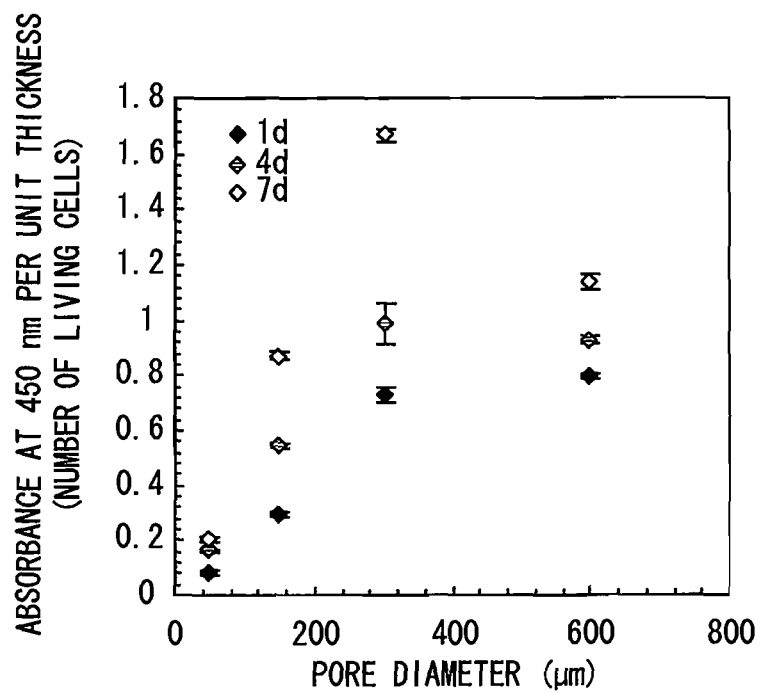
FIG. 11 is a graph illustrating results obtained by culturing Saos-2 in a state that SUS316L porous thin plates having different average pore diameters are vertically left still, respectively, and measuring the number of living cells by the WST-1 method (Test Example 6)

Next, the cells were cultured for 1, 4, 7 days in an incubator under the environment of 95% air+5% carbon dioxide gas at 37° C., and then the number of living cells was measured by the WST-1 method. The evaluation results are illustrated in FIG. 11.

Test Example 7

In 2 mL of a cell culture medium (D-MEM+10 weight % FBS), about 100,000 of Saos-2 were sowed using a tissue culture microplate having 12 holes, and preliminarily cultured for 1 day in an incubator under the environment of 95% air+5% carbon dioxide gas at 37° C.

Figure 12:
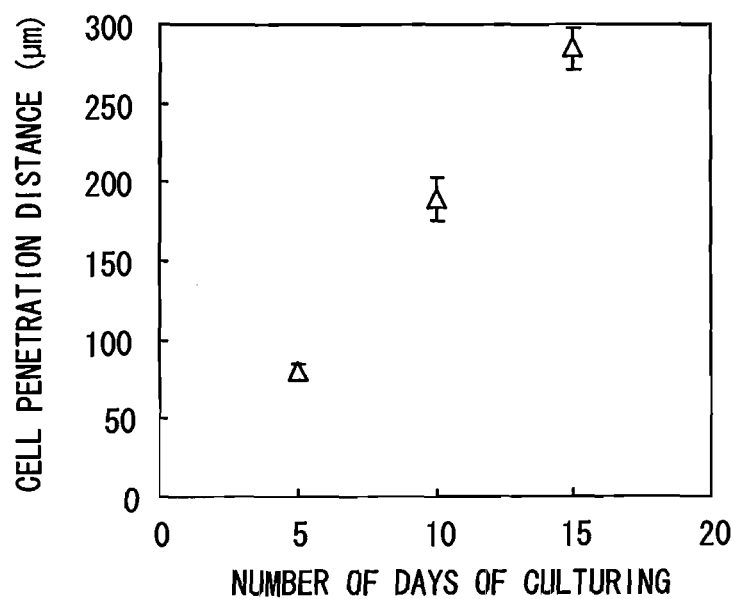
FIG. 12 is a graph illustrating results obtained by bringing a pure titanium porous thin plate in contact with cells uniformly adhered to and proliferated in a bottom surface of a cell culture microplate, sequentially performing culturing and fluorescent staining, and measuring a cell penetration distance by the confocal microscope (Test Example 7)

Then, a pure titanium porous thin plate having a three-dimensionally-open pore structure (average pore diameter of 150 μm, porosity of 89%, thickness of 0.5 mm, angle of 11 mm) was left still on the cells. The cells were cultured again for 5, 10, 15 days in an incubator under the environment of 95% air+5% carbon dioxide gas at 37° C., fixed by a 4 volume % formalin buffer solution, and then stained with a fluorescent dye (Texas Red). The cells were observed by the confocal microscope. A distance between the cell penetrated into the innermost portion and a surface of the porous thin plate was measured. The evaluation results are illustrated in FIG. 12.

Test Example 8

In 2 mL of a cell culture medium (D-MEM+10 weight % FBS), about 100,000 of Saos-2 were sowed using a tissue culture microplate having 12 holes, and preliminarily cultured for 1 day in an incubator under the environment of 95% air+5% carbon dioxide gas at 37° C.

Figure 13:
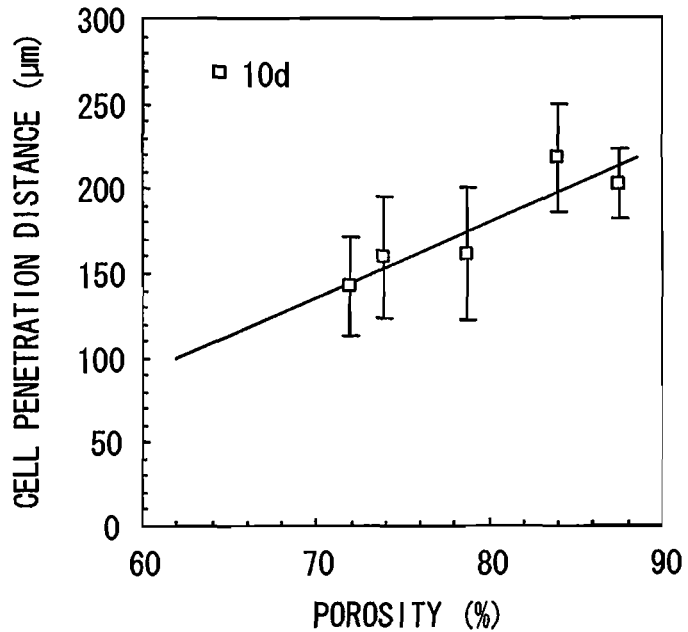
FIG. 13 is a graph illustrating results obtained by bringing pure titanium porous thin plates having different porosities in contact with cells uniformly cultured and proliferated in a bottom surface of a cell culture microplate, sequentially performing culturing and fluorescent staining, and measuring a cell penetration distance by the confocal microscope (Test Example 8)

Then, 3 pure titanium porous thin plates having a three-dimensionally-open pore structure, each of which has a different porosity, (average pore diameter of 50 μm, angle of 11 mm; porosities of 87.5%, 84.0%, 78.7%, 71.9%; thicknesses of 0.34 mm, 0.29 mm, 0.22 mm, 0.20 mm in an order of increasing the porosity) were left still on the cells. The cells were cultured again for 10 days in an incubator under the environment of 95% air+5% carbon dioxide gas at 37° C., fixed by a 4 volume % formalin buffer solution, and then stained with a fluorescent dye (Texas Red). The cells were observed by the confocal microscope. A distance between the cell penetrated into the innermost portion and a surface of the porous thin plate was measured. The evaluation results are illustrated in FIG. 13.

Test Example 9

In a tissue culture microplate having 12 holes (without cell connectivity process), a pure titanium porous thin plate 91 having a three-dimensionally-open pore structure (average pore diameter of 150 μm, porosity of 89%, thickness of 0.5 mm, angle of 11 mm) and a pure titanium nonporous thin plate 91 (thickness of 0.5 mm, angle of 11 mm) were vertically-installed using a silicon tube 92, as illustrated in FIG. 9, and about 100,000 of Saos-2 were sowed in 2 mL of a cell culture medium (D-MEM+10 weight % FBS).

Figure 16:
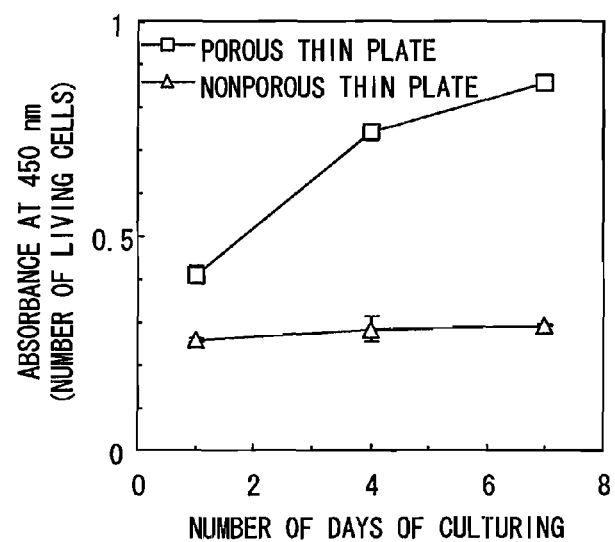
FIG. 16 is a graph illustrating results obtained by culturing Saos-2 in a state that a pure titanium porous thin plate and a pure titanium nonporous thin plate are vertically left still and measuring the number of living cells by the WST-1 method (Test Example 9).

Next, the cells were cultured for 1, 4, and 7 days in an incubator under the environment of 95% air+5% carbon dioxide gas at 37° C., and then the number of living cells was measured by the WST-1 method (color development detection). The evaluation results are illustrated in FIG. 16.

Example 3

In 2 mL of a cell culture medium (D-MEM+10 weight % FBS), about 100,000 of human osteosarcoma-derived cells Saos-2 were sowed using a tissue culture microplate having 12 holes, and preliminarily cultured for 1 day in an incubator under the environment of 95% air+5% carbon dioxide gas at 37° C.

Figure 14:
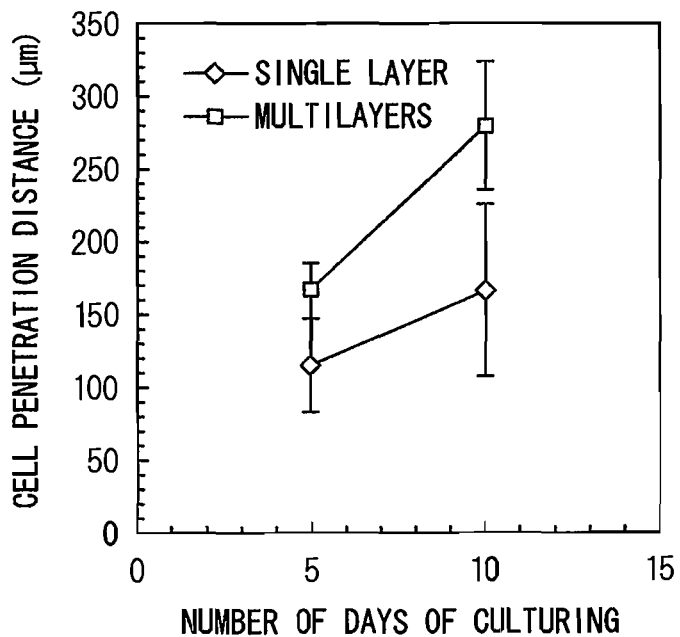
FIG. 14 is a graph illustrating results obtained by bringing a pure titanium porous joining body and a single-layer joining body in contact with cells uniformly cultured and proliferated in a bottom surface of a cell culture microplate, sequentially performing culturing and fluorescent staining, and measuring a cell penetration distance by the confocal microscope (Example 3)

Then, a multilayer-joining body to which a pure titanium porous body prepared in the same manner as in Example 2 was joined; and a pure titanium porous thin plate prepared in the same manner as above (average pore diameter of 50 μm, porosity of 79.8%, thickness of 0.3 mm) were bonded to a pure titanium foil member (thickness of 0.03 mm) and subjected to the diffusion joining, and thus a sample (hereinafter, referred to as 'single-layer joining body) was prepared. The sample was cut at an angle of 11 mm, and then subjected to the acetone cleaning and sterilization. The sample was left still on the cells so that a side bonded to the foil was an upper side. The cells were cultured again for 5, and 10 days in an incubator under the environment of 95% air+5% carbon dioxide gas at 37° C., fixed by a 4 volume % formalin buffer solution, and then stained with a fluorescent dye (Texas Red). The cells were observed by the confocal microscope. A distance between the cell penetrated into the innermost portion and the multilayer-joining body and a distance between the cell penetrated into the innermost portion and a surface of the single-layer joining body were measured. The evaluation results are illustrated in FIG. 14.

Test Example 10

A pure titanium porous thin plate having a three-dimensionally-open pore structure (average pore diameter of 150 µm, porosity of 89%, thickness of 0.5 mm, angle of 11 mm) was left still on a silicon rubber O-ring disposed in a bottom portion of a tissue culture microplate having 12 holes, and about 100,000 of human osteosarcoma-derived cells Saos-2 were sowed in 2 mL of a cell culture medium (D-MEM+10 weight % FBS).

Next, the cells were preliminary cultured for 1 day in an incubator under the environment of 95% air+5% carbon dioxide gas at 37° C., and then the cell culture medium was replaced with another one containing 0.5 mM of β-glycerophosphate and 50 µg/mL of L-ascorbic acid.

Figure 15:
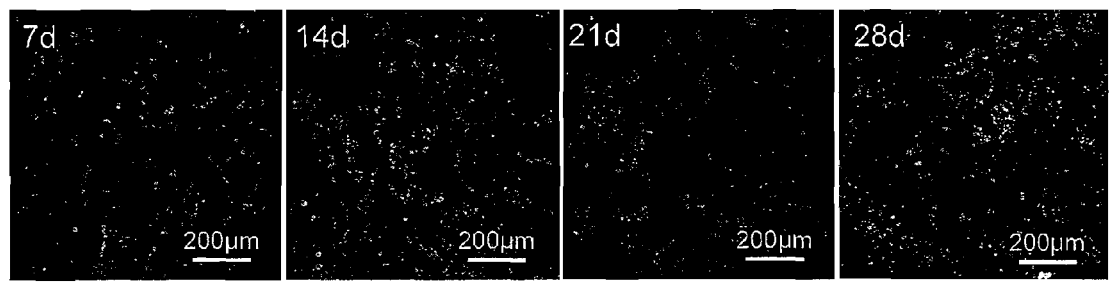
FIG. 15 illustrates images obtained by culturing Saos-2 in a pure titanium porous thin plate and observing a calcified state by the confocal microscope (Test Example 10)

Then, after the cells were cultured again for 7, 14, 21, and 28 days, calcium was labeled by replacing the cell culture medium with further another one containing 1 µg/mL of calcein and performing 4-hour culturing. After fixation using a 4 volume % formalin buffer solution, a calcified state was observed by the confocal microscope. The evaluation results are illustrated in FIG. 15.

Results of Living Tissue Connectivity Evaluation

Test Examples 5 to 8

From FIG. 8, it was confirmed that as for the pure titanium porous thin plate, the cells were adhered to and spread to the surface of the pure titanium porous thin plate and the internal bridge portion, and the cells were successfully proliferated as the number of days of culturing increased.

From FIG. 11, it was also confirmed that as for a SUS316L porous thin plate having any pore diameter, the number of living cells increased as the number of days of culturing increased. Further, it was confirmed that as for the SUS316L porous thin plates having a pore diameter equal to or less than 300 µm, the larger the pore diameter, the more the number of living cells.

In addition, it was confirmed that in the SUS316L porous thin plate having a pore diameter of 600 µm, the number of living tissue after 1-day culturing was the same as that in the SUS316L porous thin plate having a pore diameter of 300 µm, but the cell proliferation rate thereafter tended to be lower than that in the SUS316L porous thin plate having a pore diameter of 300 µm.

From FIG. 12, it was confirmed that the cells were penetrated into the porous thin plate and grown therein as the number of days of culturing increased.

From FIG. 13, it was confirmed that the cell penetration distance increased and the cell penetration tended to be facilitated as the porosity increased.

From FIG. 16, it was confirmed that the cells were not adhered to the nonporous thin plate and thus the cell proliferation was not observed, but the cells were adhered to, and proliferated in the internal bridge portion and the like of the porous thin plate.

As described above, from the results of Test Examples 5 to 9, it was confirmed that the metallic porous thin plate, which was used for the evaluations and used in the invention, had excellent connectivity with living tissue, and the cell penetration tended to be facilitated as the pore diameter or the porosity increased.

Test Example 10

From FIG. 15, it was confirmed that calcification as a first step for bone formation occurred in the pure titanium porous thin plate and the internal bridge portion. Further, it was confirmed that the calcification proceeded as the culturing proceeded for 14, 21, 28 days not for 7 days.

The sample after 28-day culturing with the calcium labeled by the fluorescent dye (Texas Red) was observed by the confocal microscope at high magnification. As a result, it was confirmed that the calcification occurred around the cells adhering to the surface of the pure titanium porous thin plate and the internal bridge portion.

From the above-described results, it was confirmed that the penetration and proliferation properties of the cells into the metallic porous thin plate used in the invention were important for the calcification and the bone formation thereafter.

Examples 2 and 3

From FIG. 10, it was confirmed that the cells were successfully grown as the number of days of culturing increased.

From FIG. 14, it was confirmed that in any sample, the cell penetration distance increased as the number of days of culturing increased. In addition, it was confirmed that the cell penetration distance was longer and the cell penetration was easier than employing the multilayer-joining body than the single-layer joining body (sample in which one surface was joined to foil).

As described above, from the results of Examples 2 and 3, it was confirmed that as for the multilayer-joining bodies of the Examples according to the invention, a penetration property of the cells was facilitated by forming the porous thin plates having different pore diameters and porosities into multilayers as compared with in the case of single layer.

According to the invention, a medical device having excellent connectivity with living tissue can be provided by being able to join a metallic porous body in which a metallic porous thin plate is multilayered as a medical device surface modification member having excellent connectivity with the living tissue to a surface of the main body of a medical device with a high joining strength. Further, a surface modification method for the medical device by which the connectivity of the medical device with the living tissue can be substantially improved can be provided by being able to easily join the metallic porous thin plate as the medical device surface modification member having excellent connectivity with the living tissue to the surface of the main body of a medical device having various surface shapes with a high joining strength.

The invention claimed is:

1. A medical device comprising:
a main body which is an artificial prosthetic member made of metal or ceramics; and
a metallic porous sintered body joined to at least a part of a surface of the main body,
wherein the metallic porous sintered body is made of a sintered metal powder and includes a plurality of metallic porous thin layers including a first thin layer joining to the main body and a second thin layer coming in contact with living tissue,
a porosity of the first thin layer is lower than the second thin layer,
the porosity of each of the metallic porous thin layers is in the range of 40 to 97%,
each of the first and second porous thin layers is prepared by molding a slurry, which contains a metal powder and a foaming agent, into a sheet shape by a doctor blade method, subjecting the slurry to a foaming process, drying the slurry, and defatting and sintering the resulting compact,
an average pore diameter in the first and the second thin layers is in the range of 20 to 800 μm,
each of the first and second thin layers has a three-dimensionally-open pore structure in a substantially spherical shape defined by foams formed by an action of the foaming agent in the foaming process, and
a specific surface area of each of the first and the second thin layers is in a range of 0.01 to 0.5 m$^2$/g.

2. The medical device according to claim 1,
wherein the metallic porous sintered body includes at least one metal selected from pure titanium, a titanium alloy, stainless steel, a cobalt chrome alloy, tantalum, niobium, and an alloy thereof.

3. The medical device according to claim 2,
wherein the metal is the same kind as used for the main body of a medical device.

4. The medical device according to claim 1,
wherein a surface of a skeleton including the sintered metal powder of the metallic porous sintered body is covered with an inorganic compound having biocompatibility.

5. The medical device according to claim 4,
wherein the inorganic compound is selected from calcium phosphate, hydroxyapatite, and metal oxide including titanium oxide.

6. The medical device according to claim 1,
wherein a porosity of the first thin plate is in a range of 50 to 85%, and a porosity of the second thin plate is in the range of 80 to 95%.

7. The medical device according to claim 1,
wherein each of the first and second thin layers contains multiple pores that are disposed at a different level in a thickness direction.

8. The medical device according to claim 1,
wherein no pore of the three-dimensionally-open pore structure extends completely through the first or second porous thin layers.

* * * * *